United States Patent [19]

Portman

[11] Patent Number: 5,585,101
[45] Date of Patent: Dec. 17, 1996

[54] METHOD TO IMPROVE PERFORMANCE DURING EXERCISE USING THE CIWUJIA PLANT

[75] Inventor: Robert Portman, Woodbridge, N.J.

[73] Assignee: PacificHealth Laboratories, Inc., Woodbridge, N.J.

[21] Appl. No.: 574,686

[22] Filed: Dec. 19, 1995

[51] Int. Cl.⁶ .................................................. A61K 35/78
[52] U.S. Cl. ........................................................ 424/195.1
[58] Field of Search ........................................... 424/195.1

[56] References Cited

U.S. PATENT DOCUMENTS

| | | | |
|---|---|---|---|
| 4,154,822 | 5/1979 | Polimeni et al. | 514/54 |
| 4,315,927 | 2/1982 | Evans | 514/188 |
| 4,670,264 | 6/1987 | Warren et al. | 424/195.1 |
| 4,695,549 | 9/1987 | Grabitz | 435/267 |
| 4,698,360 | 10/1987 | Masquelier | 514/456 |
| 5,096,708 | 3/1992 | Gohla et al. | 424/195.1 |
| 5,096,712 | 3/1992 | Wurtman | 424/422 |
| 5,270,297 | 12/1993 | Paul et al. | 514/23 |
| 5,360,821 | 11/1994 | Leung | 514/563 |
| 5,403,921 | 4/1995 | Montner et al. | 424/722 |
| 5,422,346 | 6/1995 | Mitchell et al. | 514/54 |

OTHER PUBLICATIONS

Medline Medical Search.

*Primary Examiner*—John W. Rollins

[57] ABSTRACT

The invention relates to method for enhancing stamina and physical performance during exercise and for enhancing recovery following cessation of exercise. The method consists of administering to human beings a predetermined dosage of an extract of the root and rhizome ciwujia (Latin names of ciwujia are Radix acanthopanax senticosus or Radix eleutherococcus senticosus).

16 Claims, 9 Drawing Sheets

EFFECT OF CIWUJIA ON RECOVERY OF LACTIC ACID LEVELS (mM)

| TIME (min) | PRE-CIWUJIA | POST-CIWUJIA | % DECREASE |
|---|---|---|---|
| 0 | 14.73 | 10.01 | 32.04 |
| 5 | 13.52 | 8.8 | 34.91 |
| 15 | 9.84 | 6.49 | 34.04 |

*FIG. 7*

EFFECT OF CIWUJIA ON HEART RATES (BEATS/MIN) AT VARIOUS ENERGY LOADS

| LOAD | PRE-CIWUJIA MEAN | POST-CIWUJIA MEAN |
|---|---|---|
| 0 | 81.14 | 85.65 |
| 60 | 110.53 | 105.27 |
| 90 | 124.25 | 118.46 |
| 120 | 138.50 | 131.17 |
| 150 | 155.88 | 145.04 |
| 180 | 166.54 | 161.71 |
| 210 | 174.90 | 172.38 |

*FIG. 8*

EFFECT OF CIWUJIA ON HEART RATE FOLLOWING EXERCISE

| TIME (min) | PRE-CIWUJIA | POST-CIWUJIA | % DECREASED |
|---|---|---|---|
| 0 | 174.9 | 172.3 | 1.4 |
| 5 | 128 | 111 | 13.2 |
| 10 | 120.7 | 104.4 | 13.6 |
| 15 | 110.1 | 97.5 | 11.5 |

*FIG. 9*

EFFECT OF CIWUJIA ON PRE-AND POST-EXERCISE HEART RATES

| TIME (min) | PRE-CIWUJIA (%) | POST-CIWUJIA (%) |
|---|---|---|
| PRE-EXERCISE VALUE | 100 | 100 |
| 0 | 215 | 199 |
| 5 | 157 | 128 |
| 10 | 148 | 120 |
| 15 | 135 | 113 |

*FIG. 10*

EFFECT OF CIWUJIA ON RESPIRATORY QUOTIENTS
AT VARIOUS ENERGY LOADS

| LOAD | PRE-CIWUJIA MEAN | POST-CIWUJIA MEAN | CHANGE |
|---|---|---|---|
| 0 | 0.94 | 0.78 | −0.16 |
| 60 | 0.94 | 0.91 | −0.03 |
| 90 | 0.92 | 0.89 | −0.03 |
| 120 | 0.98 | 0.88 | −0.10 |
| 150 | 1.06 | 0.88 | −0.18 |
| 180 | 1.07 | 0.86 | −0.21 |
| 210 | 1.05 | 0.86 | −0.19 |
| MEAN | 0.99 | 0.86 | −0.13 |

FIG. 11

| | PRE-CIWUJIA | | POST-CIWUJIA | | % INCREASE FAT METABOLISM |
|---|---|---|---|---|---|
| LOAD (WATTS) | % CARBO UTILIZATION | % FAT UTILIZATION | % CARBO UTILIZATION | % FAT UTILIZATION | |
| 60 | 79.9 | 20.1 | 69.9 | 30.1 | 10.0 |
| 90 | 73.2 | 26.8 | 63.6 | 36.7 | 10.1 |
| 120 | 93.2 | 6.8 | 59.9 | 40.1 | 33.3 |
| 150 | 100 | 0 | 59.9 | 40.1 | 40.1 |
| 180 | 100 | 0 | 53.3 | 46.7 | 46.7 |
| 210 | 100 | 0 | 53.3 | 46.7 | 46.7 |
| MEAN | 96.6 | 3.4 | 53.5 | 46.7 | 43.3 |

FIG. 12

EFFECT OF CIWUJIA ON $VO_2$, $VCO_2$ AND EE
(ENERGY EXPENDITURE) AT 4 mM LACTIC ACID

| PARAMETER | PRE-CIWUJIA MEAN | POST-CIWUJIA MEAN | CHANGE |
|---|---|---|---|
| $VO_2$ | 1.99 | 2.12 | ↑ 7% |
| $VCO_2$ | 2.0 | 1.85 | ↓ 7.5% |
| EE | 41.48 | 42.85 | ↑ 3.3% |

*FIG. 13*

EFFECT OF CIWUJIA ON ANAEROBIC POWER TOLERANCE

| PRE-CIWUJIA WEEK 0 | POST-CIWUJIA WEEK 2 | % INCREASE |
|---|---|---|
| 134.0 | 150.6* | 12.4% |

EFFECT OF CIWUJIA ON FAT METABOLISM AND % LEAN
BODY MASS AT VARIOUS EXERCISE REGIMEN

EXAMPLE A

| WEIGHT | EXERCISE LEVEL | ENERGY EXPENDITURE CONSTANT | TIMES/ WEEK | EXERCISE DURATION | FAT/CARBO RATIO AS FUNCTION OF DURATION |
|---|---|---|---|---|---|
| 170 | RUNNING 7 MIN/MILE | .109 CAL/MIN/LB | 4 | 30 | .35/.65 |

|  | EXERCISE REGIMEN | EXERCISE REGIMEN WITH CIWUJIA |
|---|---|---|
| TOTAL ENERGY EXPENDITURE | 2223 | 2223 |
| CARBOHYDRATE CALORIES METABOLIZED | 778 | 400 |
| FAT CALORIES METABOLIZED | 1444 | 1822 |
| FAT CALORIES METABOLIZED OVER 12 MONTHS | 75,088 | 94,744 |
| # OF FAT POUNDS METABOLIZED OVER 12 MONTHS | 21.4 | 27.0 |

% INCREASE IN LEAN BODY MASS = 3.3%

FIG. 15A

EFFECT OF CIWUJIA ON FAT METABOLISM AND % LEAN
BODY MASS AT VARIOUS EXERCISE REGIMEN

EXAMPLE B

| WEIGHT | EXERCISE | EXERCISE LEVEL | ENERGY EXPENDITURE CONSTANT | TIMES/WEEK | EXERCISE DURATION | FAT/CARBO RATIO AS FUNCTION OF DURATION |
|---|---|---|---|---|---|---|
| 150 | BICYCLING | 20 MPH | .105 CAL/MIN/LB | 5 | 20 | .38/.62 |

|  | EXERCISE REGIMEN | EXERCISE REGIMEN WITH CIWUJIA |
|---|---|---|
| TOTAL ENERGY EXPENDITURE | 1575 | 1575 |
| CARBOHYDRATE CALORIES METABOLIZED | 598 | 299 |
| FAT CALORIES METABOLIZED | 976 | 1275 |
| FAT CALORIES METABOLIZED OVER 12 MONTHS | 46,752 | 66,300 |
| # OF FAT POUNDS METABOLIZED OVER 12 MONTHS | 13.3 | 18.9 |

% INCREASED IN LEAN BODY MASS = 3.7%

*FIG. 15B*

METHOD TO IMPROVE PERFORMANCE DURING EXERCISE USING THE CIWUJIA PLANT

FIELD OF THE INVENTION

The present invention relates to a method to improve physical performance and stamina during exercise and for enhancing recovery following cessation of exercise. The method comprises administration to human beings of a dietary supplement composed of a predetermined dose of an extract from the root and rhizome, ciwujia (Latin names of ciwujia are Radix acanthopanax senticosus or Radix eleutherococcus senticosus).

BACKGROUND OF THE INVENTION

It has long been desirable to improve physical performance during exercise. Basically three different approaches have been explored. These include the use of: (1) anabolic agents, (2) nutritional intervention, (3) and agents to optimize the nutritional source of energy during exercise. The use of anabolic agents to enhance performance has been extensively studied. The most well known agents of this group are anabolic steroids or testosterone derivatives. Anabolic steroids have been shown to increase muscle mass, improve recovery following exercise and improve overall strength. These products, however, are associated with serious side effects. Anabolic steroids can cause interrupted growth, virilization, and disorders of the reproductive system and liver. They can also cause serious psychological disorders. As a result of these side effects use of anabolic steroids to improve physical performance is considered highly undesirable.

Nutritional intervention has been directed primarily toward the utilization of carbohydrate and fat during exercise. Carbohydrate represents the rate limiting constituent during exercise. During higher exercise levels there is a shift toward greater carbohydrate use by muscle cells. Depletion of intramuscular stores of glycogen is almost always coincident with muscular exhaustion, even when there is sufficient fat stores still available to the muscle for fuel. Muscle depletion of carbohydrate stores during exercise also produces a metabolic shift from aerobic to an anaerobic state. A consequence of this anaerobic shift is a build-up of lactic acid. Lactic acid build-up is the primary reason for muscle fatigue and soreness during exercise. Researchers have found that increasing the consumption of carbohydrate ("carbohydrate loading") prior to exercise can increase the amount of muscle glycogen available during exercise. To derive the full benefits of carbohydrate loading a complicated regimen must be followed which includes critical attention to timing.

The third approach involves use of agents to optimize the cellular utilization of carbohydrate, fat and oxygen during exercise. Products that spare muscle glycogen will theoretically improve physical performance by delaying depletion of intramuscular stores of glycogen and the resulting lactic acid build-up. Investigators have shown that caffeine produces a carbohydrate sparing effect by increasing lipolysis (the break down of fat) during exercise. Athletes administered caffeine prior to exercise demonstrate an increase in stamina, an increase in the metabolism of fat and an increase in the lactate threshold in relation to workload. Caffeine is also associated with a number of undesirable side effects including increasing heart rate, stimulation of the central nervous system, increasing diuresis, raising metabolic rate and raising body temperature. These side effects negatively impact physical performance.

There is a definite need in the art for a product that will enhance physical performance during exercise without the limitations and side effects associated with existing products and regimens. In view of the foregoing it is the object of this invention to provide a safe, simple method that will significantly enhance stamina and physical performance during exercise and speed recovery following the cessation of exercise.

DESCRIPTION OF THE PRIOR ART

Products to enhance stamina and performance which are natural herbal products or synthetically made products having various organic structures and metabolic functions have been disclosed in the prior art. For example, U.S. Pat. Nos. 4,154,822; 4,670,264; 4,695,549; 4,698,360; 5,096,708; 5,096,712; 5,270,297; 5,360,821; 5,403,921; and 5,4222, 346 disclose therapeutic drugs, chemicals, herbal products and the like for improving and enhancing metabolic functions in animal and human subjects which can further improve the users stamina, energy or performance.

In addition, human and animal studies have been published on the effect of ciwujia on histamine release, on the reduction of malignant arrhythmias, on aging, on hypoglycemia, on reducing the size of an acute myocardial infarction, on stimulation of the immune system, on increasing tolerance to hypoxia and elevated temperatures, on increasing tolerance to stress and on modestly increasing swimming time to exhaustion of laboratory rats.

None of the aforementioned prior art patents, or published studies disclose the use of an extract or concentrate from the ciwujia root or rhizome for enhancing stamina or physical performance of human subjects during exercise.

Previously published literature has shown that ciwujia is an exceedingly safe natural product. Ciwujia has been administered to human beings in doses of 3-27 gm/day without any reported side effects. In addition, ciwujia has been administered to laboratory animals at 60 to 200 times the recommended human dose without producing any abnormalities or untoward effects.

Accordingly, it is an object of the present invention to provide a product which will increase stamina and physical performance of humans during exercise using an extract from the ciwujia plant, including the root, stem, bark, fruit, etc.

Another object of the present invention is to provide a product to be used for improving endurance of a human during exercise by administering a predetermined dosage of an extract of ciwujia.

Another object of the present invention is to provide a product for sparing muscle glycogen of a human during exercise by administering a predetermined dosage of an extract of ciwujia.

Another object of the present invention is to provide a product for increasing fat breakdown (lipolysis) of a human during exercise by administering a predetermined dosage of an extract of ciwujia.

Another object of the present invention is to provide a product for increasing the percent of lean body mass when taken in conjunction with an exercise regimen by administering a predetermined dosage of an extract of ciwujia.

Another object of the present invention is to provide a product that will increase the lactate threshold in relationship to workload of a human during exercise by administering a predetermined dosage of an extract of ciwujia.

Another object of the present invention is to provide a product that increases oxygen consumption of a human during exercise by administering a predetermined dosage of an extract of ciwujia.

Another object of the present invention is to provide a product that will enhance recovery of heart rate to pre-exercise levels of a human being by administering a predetermined dosage of an extract of ciwujia.

Another object of the present invention is to provide a product that will enhance recovery of lactic acid levels to pre-exercise levels of a human being by administering a predetermined dosage of an extract of ciwujia.

Another object of the present invention is to provide a product that will increase the anaerobic threshold of a human being during exercise by administering a predetermined dosage of an extract of ciwujia.

SUMMARY OF THE INVENTION

In accordance with the present invention, there is provided a method for enhancing stamina and performance during exercise using the extract of the ciwujia plant. More specifically, by administering a predetermined dosage of an extract of the ciwujia plant to human subjects there are a number of positive effects based on several clinical and laboratory studies. The positive results of using ciwujia to improve performance and stamina during exercise include at least the following:

1. Improving the endurance, stamina, and performance of humans during exercise;
2. Delaying the onset of fatigue during exercise;
3. Increasing oxygen ($O_2$) consumption during exercise;
4. Increasing the anaerobic power threshold during exercise;
5. Sparing of muscle glycogen during exercise;
6. Increasing fat metabolism during exercise which increases the percent of lean body mass;
7. Returning the heart rate to normal following the cessation of exercise;
8. Decreasing the lactate threshold at various energy work loads during exercise; and
9. Returning the lactic acid level to normal following the cessation of exercise.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein:

FIG. 7 is a table showing the effect of ciwujia on lactic acid recovery following exercise;

FIG. 8 is a table showing the effect of ciwujia on heart rate at various energy loads;

FIG. 9 is a table showing the effect of ciwujia on heart rate recovery following exercise;

FIG. 10 is a table showing the effect of ciwujia on pre and post exercise heart rates;

FIG. 11 is a table showing the effect of ciwujia on respiratory quotients at various energy loads;

FIG. 12 is a table showing the effect of ciwujia on carbohydrate and fat utilization at various energy loads;

FIG. 13 is a table showing the effect of ciwujia on oxygen and energy expenditure at 4 MM lactic acid;

FIG. 14 is a table showing the effect of ciwujia on anaerobic power tolerance; and FIG. 15 is a table showing the effect of ciwujia on fat metabolism and percent lean body mass at various exercise regimens.

DETAIL DESCRIPTION OF THE PREFERRED EMBODIMENT

The preferred embodiment of the present invention provides a method which uses an extract of ciwujia (Latin names of ciwujia are Radix acanthopanax senticosus or Radix eleutherococcus senticosus) to enhance stamina, increase oxygen intake, increase the lactate threshold at various energy loads, increase anaerobic threshold and increase fat metabolism during exercise. The preferred embodiment of the present invention also provides a method to speed recovery following cessation of exercise as measured by restoration of heart rate and lactic acid to pre-exercise levels. According to the present invention it has beneficially found that an extract from the ciwujia plant contains natural compounds which have a positive effect on physical performance of humans during exercise.

The extract of the ciwujia plant is constituted by grinding the root, stem, bark, leaf, fruit, etc. and removing the active constituents through a water extraction process. The dosage range for an extract of a ciwujia plant to be used by humans have an overall general range of 200 to 1600 mg per day, a preferred range of 400 to 1200 mg per day and a specific daily dosage of 800 mg per day.

EXAMPLE 1

Figure 1:
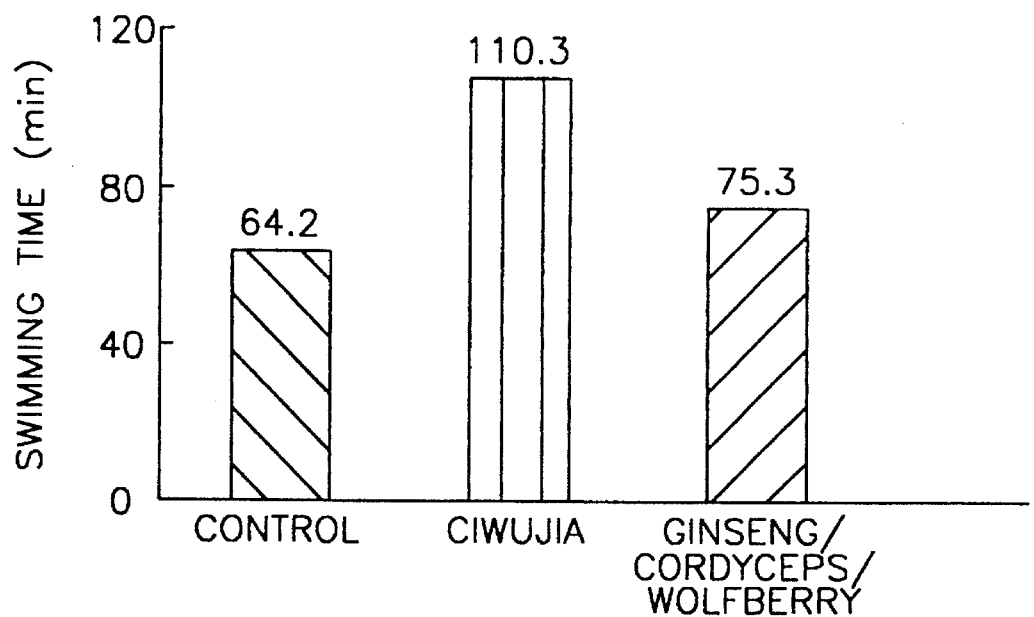
FIG. 1 is a graph showing results of ciwujia versus a combination of other herbs.

To determine if ciwujia increased endurance a trial was conducted using the mouse swimming time model. In this trial, test mice had there diet supplemented with a specific herb or herb combination for one week. After one week their swimming time to exhaustion was measured. Nine (9) mice were in each group. Ciwujia (400 mg) was compared to a herb combination consisting of ginseng (100 mg), cordyceps (40 mg) and wolfberry (50 mg). The results are shown in FIG. 1. The times for the three groups were as follows: control-64.2 minutes; ciwujia group 110.3 minutes; herb combination 75.3 minutes. Ciwujia extended swimming time over the control group by 72% and the combination herb group by 46.5%. These differences were significant ($P<0.05$).

EXAMPLE 2

Figure 2:
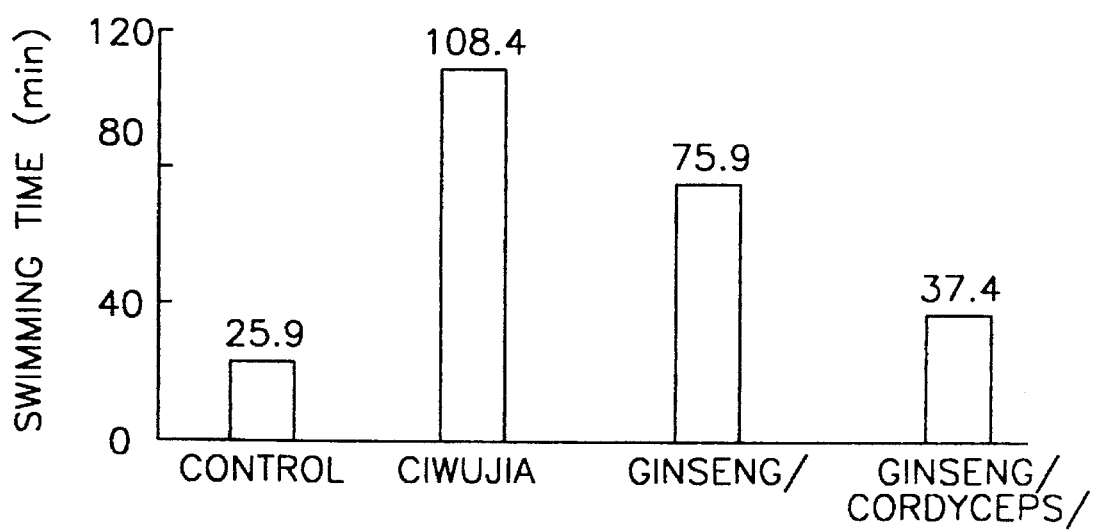
FIG. 2 is a graph showing the results of ciwujia versus ginseng and a ginseng cordyceps combination.

This study compared ciwujia (800 mg) to ginseng (400 mg) and a combination of ginseng (400 mg)+cordyceps (200 mg). Fourteen (14) mice were used in each group. The same protocol was followed as outlined in EXAMPLE 1. The results are shown in FIG. 2. The ciwujia group outperformed the control group by 318% (P<0.05); the ginseng group by 43%; and the ginseng and cordyceps combination by 190%. This study showed that ciwujia is superior to ginseng in improving endurance. The study also suggested that combining performance enhancing herbs which are effective alone may result in a lower activity than that seen when the herb is administered by itself.

EXAMPLE 3

Figure 3:
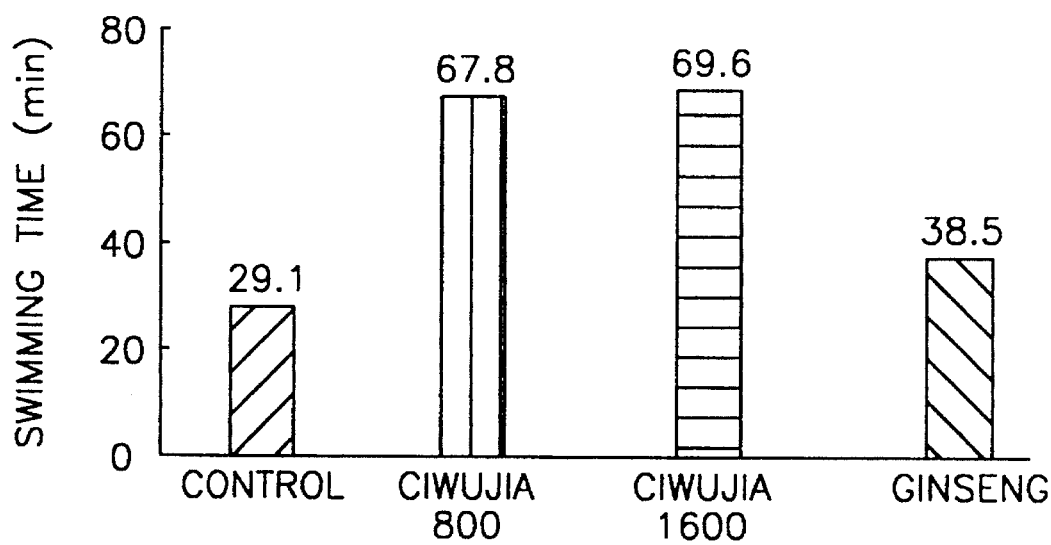
FIG. 3 is a graph showing the results of varying doses of ciwujia versus ginseng.

This study compared the effect of ciwujia at different doses versus a control and a ginseng group. There were fifteen (15) animals per group. The same protocol was followed as outlined in EXAMPLE 1. The results are shown in FIG. 3. The study showed there was little difference between the effect of ciwujia 800 mg and ciwujia 1600 mg. Ciwujia extended swimming time test over the control by 133% and over ginseng (200 mg) by 76%.

EXAMPLE 4

Figure 4:
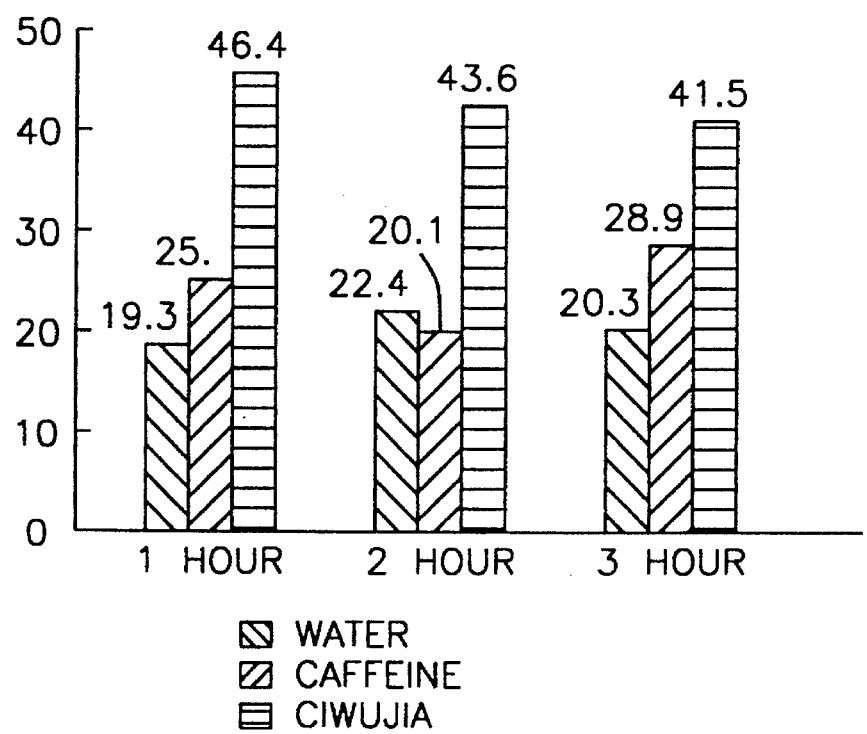
FIG. 4 is a chart comparing the effect of ciwujia to caffeine when administered 1 to 3 hours prior to testing.

In this study mice were administered tap water, caffeine (200 mg) or ciwujia (800 mg) either one, two or three hours prior to measuring swimming times. Fifteen (15) mice were in each group. The results shown in FIG. 4 revealed that ciwujia significantly improved mouse swimming times when administered one, two or three hours prior to testing. The results also showed that ciwujia was superior to caffeine in improving swimming times when administered one, two or three hours prior to testing.

EXAMPLE 5

This study was conducted on human subjects. The objective was to measure the effect of ciwujia on stamina and performance. Eight (8) healthy male subjects ranging from 25–35 years old were given a placebo for three days. The subjects were then administered 800 mg of the ciwujia extract for two weeks. On days three and seventeen the subjects underwent aerobic performance assessment using a Monark power bike in which power was increased from 60 to 210 watts at 30 watt intervals. Each interval lasted three minutes. At the end of each interval peripheral blood was collected to measure lactic acid and anaerobic tolerance. Peripheral blood was collected at five to ten minutes after the last interval. Subjects had continuous heart rate VO2 and CO2 monitoring. Results of the exercise physiology studies performed are depicted in FIGS. 5–11.

Figure 5:
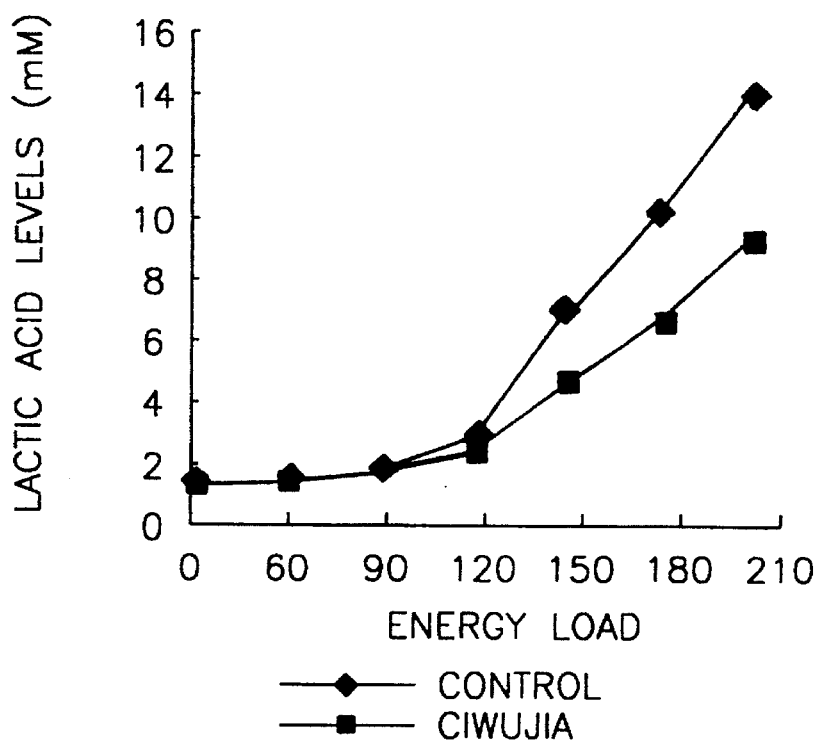
FIG. 5 is a graph showing the effect of ciwujia on lactic acid levels at various energy loads.
Figure 6:
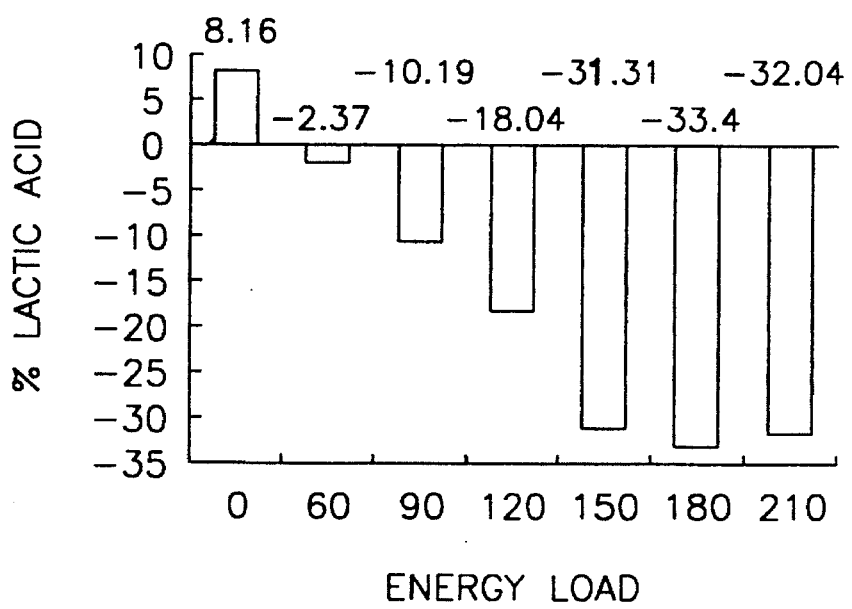
FIG. 6 is a graph showing the effect of ciwujia on lactic acid levels at various energy loads.

FIGS. 5 and 6 show the effect of ciwujia on the lactate threshold at various energy loads. The effect of ciwujia was more pronounced at higher energy loads. At 150 watts there was a 31% drop in lactic acid levels when compared to control. At 180 watts the decrease was 33% and at 210 watts the decrease was 32% when compared to control.

FIG. 7 shows the effect of ciwujia on lactic acid recovery. At all three measurement points following cessation of exercise the post ciwujia lactic acid levels were 32 to 35 percent lower then the control values.

FIG. 8 shows the effect of ciwujia on heart rate at various energy loads. There was a slight decrease following administration of ciwujia at all energy loads. This difference appeared more significant at higher energy loads.

FIGS. 9 shows the effect of ciwujia on heart rate following exercise. When compared to control, heart rates in the ciwujia group were 11 to 13 percent lower.

FIG. 10 shows the effect of ciwujia on pre and post exercise heart rates. When the heart rate at fifteen minutes following cessation of exercise was compared to the pre-exercise level the post ciwujia value was 113% versus the pre-ciwujia value of 135%.

FIG. 11 shows the effect of ciwujia on the Respiratory Quotient with the measuring of $O_2$ intake and $CO_2$ expiration at various power loads. The mean Respiratory Quotient for the subjects pre ciwujia was 0.99. The mean Respiratory Quotient for the subjects post ciwujia was 0.86. The decline in the Respiratory Quotient indicates that ciwujia induces a metabolic shift during exercise, increasing the metabolism of fat as a muscle energy source. Based on the Respiratory Quotient data, one can calculate the percentage of carbohydrate and fat utilized for energy during exercise. It is well documented that a Respiratory Quotient of 1.0 or more indicates that 100% of the energy is being produced from muscle glycogen, and a Respiratory Quotient of 0.7 indicates that 100% of the energy is being produced from fat sources. FIG. 12 converts the Respiratory Quotient data shown in FIG. 11 into the percentage of energy derived from carbohydrate and fat at various energy loads. Following ciwujia administration, there is a mean increase of 43.3% in the energy derived from fat and a corresponding decrease in the use of carbohydrate for muscle energy source. The glycogen-sparing effect slows the buildup of lactic acid and delays muscle fatigue.

EXAMPLE 6

This study was conducted to assess anaerobic power threshold in subjects receiving ciwujia. Eight (8) healthy males participated in the trial. Using a Monark power bike, the subjects started at a low resistance which then increased to a specified load in 3 to 5 minutes. Subjects continued pedaling at their maximum strengths for 30 seconds, at which time the maximum anaerobic power was recorded. Each subject was then administered 800 mg of ciwujia for two weeks and the anaerobic assessment repeated.

According to the International Association of Sports Medicine the anaerobic threshold for blood lactic acid was assigned to 4mM. Analyses were performed to determine the differences at 4 mM of lactic acid between week 0 and week 2. The level of blood lactic acid was plotted vs power load (watts) for each subject and fitted to a third order polynomial function to determine the power level threshold at the 4 mM lactic acid level. The results are shown in FIGS. 12 and 13. After two weeks of treatment the ciwujia group showed an increase in the anaerobic power tolerance of 12.4%. This increase was highly statistically significant (P=0.02). This study also showed that there was a 7% increase in VO2 and this increase was highly significant.

EXAMPLE 7

To assess the effect of ciwujia on energy metabolism of various exercise regimens, the following analysis was conducted. Caloric expenditure/min/lb. constants have been published for a range of exercise and exercise intensities. Studies have also been published showing the ratio of carbohydrate to fat metabolism as an energy source during exercise as a function of exercise duration. Based on this information, the effect of ciwujia on carbohydrate and fat utilization during exercise can be calculated. As shown in FIG. 15, examples A and B demonstrate the effect of ciwujia on two different exercise regimens. Each example was normalized to take into account the increase in fat metabolism that occurs as the duration of physical activity increases. Example A illustrates that ciwujia would increase the number of fat pounds metabolized over a 12-month period by 5.6 lb. or an increase in percent lean body mass of 3.3%. Example B illustrates that ciwujia would increase the number of fat pounds metabolized over a 12 month period by 5.6 lb. or an increase in percent lean body mass of 3.7%.

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the invention as those of skill in the art will readily understand. Accordingly, such variations and modifications are considered to be within the purview and scope of the invention and the following claims.

What is claimed is:

1. A method to improve physical performance of a human being during exercise comprising administering to said human being a daily dosage of 200 mg to 1600 mg of an aqueous extract of the ciwujia plant.

2. A method to improve stamina, endurance and performance of a human being during exercise comprising administering to said human being a daily dosage of 200 mg to 1600 mg of an aqueous extract of the ciwujia plant.

3. A method of delaying the onset of muscle fatigue of a human being during exercise comprising administering to said human being a daily dosage of 200 mg to 1600 mg of an aqueous extract of the ciwujia plant.

4. A method to decrease the lactate threshold at various energy work loads in a human being during exercise comprising administering to said human being a daily dosage of 200 mg to 1600 mg of an aqueous extract of the ciwujia plant.

5. A method to spare muscle glycogen of a human being during exercise comprising administering to said human being a daily dosage of 200 mg to 1600 mg of an aqueous extract of the ciwujia plant.

6. A method to increase fat metabolism (lipolysis) of a human being during exercise comprising administering to said human being a daily dosage of 200 mg to 1600 mg of an aqueous extract of the ciwujia plant.

7. A method to increase the percent of lean body mass of a human being when taken as part of an exercise regimen comprising administering to said human being a daily dosage of 200 mg to 1600 mg of an aqueous extract of the ciwujia plant.

8. A method to increase the anaerobic power threshold of a human being during exercise comprising administering to said human being a daily dosage of 200 mg to 1600 mg of an aqueous extract of the ciwujia plant.

9. A method of restoring heart rate to normal of a human being following cessation of exercise comprising administering to said human being a daily dosage of 200 mg to 1600 mg of an aqueous extract of the ciwujia plant.

10. A method of restoring lactic acid levels to normal of a human being following cessation of exercise comprising administering to said human being a daily dosage of 200 mg to 1600 mg of an aqueous extract of the ciwujia plant.

11. A method to increase oxygen consumption of a human being during exercise comprising administering to said human being a daily dosage of 200 mg to 1600 mg of an aqueous extract of the ciwujia plant.

12. A method in accordance with any one of claims 1 to 11 wherein a daily dosage ranging from 400 mg to 1200 mg of an aqueous extract of the ciwujia plant is administered.

13. A method in accordance with any one of claims 1 to 11 wherein a daily dosage of 800 mg of an aqueous extract of the ciwujia plant is administered.

14. A method in accordance with any one of claims 1 to 11 wherein said daily dosage of 200 mg to 1600 mg of an aqueous extract of the ciwujia plant is administered one to three hours prior to physical exercise.

15. A method in accordance with claim 12 wherein said daily dosage of 400 mg to 1200 mg of an aqueous extract of the ciwujia plant is administered one to three hours prior to physical exercise.

16. A method in accordance with claim 13 wherein said daily dosage of 800 mg of an aqueous extract of the ciwujia plant is administered one to three hours prior to physical exercise.

* * * * *